US006870356B2

(12) United States Patent
Murray et al.

(10) Patent No.: US 6,870,356 B2

(45) Date of Patent: Mar. 22, 2005

(54) METHOD AND APPARATUS FOR VERTICAL VOLTAGE POTENTIAL MAPPING

(75) Inventors: Neal S. Murray, Hamburg, NY (US); Henry G. Kleinfelder, Jr., Orchard Park, NY (US); Kevin D. Niles, Lockport, NY (US)

(73) Assignee: S-T-N Holdings, Inc., Las Vegas, NV (US)

( * ) Notice: Subject to any disclaimer, the term of this patent is extended or adjusted under 35 U.S.C. 154(b) by 3 days.

(21) Appl. No.: 10/411,803

(22) Filed: Apr. 11, 2003

(65) Prior Publication Data

US 2004/0201381 A1 Oct. 14, 2004

(51) Int. Cl.[7] ......................... G01N 27/00; G01R 27/08

(52) U.S. Cl. ..................... 324/71.1; 324/700; 174/45 R

(58) Field of Search ................................ 324/522, 346, 324/700, 71.1–71.6, 713, 716–717; 702/33–34, 94; 204/196.06, 404; 174/3, 6, 7, 45 R

(56) References Cited

U.S. PATENT DOCUMENTS 4,228,399 A * 10/1980 Rizzo et al. ................ 324/425
5,728,943 A * 3/1998 Colter et al. .................. 73/799
6,060,877 A * 5/2000 Nekoksa .................... 324/71.1
6,155,360 A * 12/2000 McLeod ..................... 175/258
6,408,953 B1 * 6/2002 Goldman et al. ............. 175/39
6,744,265 B2 * 6/2004 Yunovich et al. ........... 324/700

OTHER PUBLICATIONS

García, J.M. Malo, and J. Uruchurtu, *Corrosion Monitoring of Electric Transmission Line Tower Legs by Electrochemical Methods*, InterCorr/96 Online Corrosion Conference, Session 4, 1996.

* cited by examiner

*Primary Examiner*—N. Le
*Assistant Examiner*—Jeff Natalini
(74) *Attorney, Agent, or Firm*—Hodgson Russ LLP

(57) ABSTRACT

A method of mapping voltage potential along a metal structural member extending underground through a range of depths comprises the steps of providing a voltage meter having positive and negative terminals, a reference electrode connected to the positive terminal, and a half-cell connected to the negative terminal; forming at least one hole in the ground alongside the structural member; contacting the reference electrode with the structural member at an above-ground location; and positioning the half-cell at a series of test points in the hole(s) and taking a series of voltage potential measurements respectively corresponding to the series of test points, wherein the test points are located at different depths. Preferably, the method further comprises the step of plotting test point depth versus voltage potential. A novel drill bit for drilling the hole through earth comprises a common wood-boring auger shank and a flat masonry-style drill bit tip.

7 Claims, 2 Drawing Sheets

METHOD AND APPARATUS FOR VERTICAL VOLTAGE POTENTIAL MAPPING

FIELD OF THE INVENTION

The present invention relates generally to the field of corrosion detection in buried structural members, in particular vertical or near vertical structural members.

DESCRIPTION OF RELATED ART

A widely used technique for locating areas of corrosion in underground metal pipelines is the Close Interval Potential Survey (CIPS). A Close Interval Potential Survey is typically performed by drilling a hole to expose a contact point on the pipeline, contacting a reference electrode to the exposed contact point, and providing a portable copper/copper sulfate ($Cu/CuSO_4$) half-cell electrode. The reference electrode is connected to the positive terminal of a voltage meter, while the portable half-cell electrode is connected by a spool of wire to the negative terminal of the voltage meter. Potential measurements are then made at three to five foot intervals along the pipeline by repositioning the half-cell on the ground above the pipeline for each measurement. The pipe-to-soil voltage potential measurements are plotted against the corresponding distance of the half-cell along the pipeline relative to the location of the reference electrode. Anomalies or peaks in the plot indicate the location of corrosion trouble spots along the pipeline, thereby enabling maintenance crews to dig in specific locations to visually observe the condition of the pipe.

The problem of corrosion in buried metal structures is not, however, confined to pipelines. For example, metal footings for transmission line towers often run vertically or near-vertically through the ground to depths of eight feet or more. Corroded footings can lead to shifting or even collapse of a tower, possibly resulting in power outage and an unsafe site. Heretofore, locating corrosion damage to these footings has involved visual inspection of the footing near the ground surface and, in some cases, digging around a footing to expose the footing for visual inspection. While the Close Interval Potential Survey technique has been used for many years in connection with lengthy pipelines, it has not been adapted for use in connection with vertical or near vertical structural members which are much shorter than pipelines and do not run substantially parallel to the ground surface as do pipelines.

It has been proposed to take a corrosion potential measurement at a single location near a transmission line footing as part of an electrochemical corrosion monitoring method that incorporates other parameters such as soil resistivity, the Tafel slope portion of the polarization curve, linear polarization resistance, and potential noise over time. See E. Garcia, J. M. Malo, and J. Uruchurtu, *Corrosion Monitoring of Electric Transmission Line Tower Legs by Electrochemical Methods*, InterCorr/96 Online Corrosion Conference, Session 4, 1996. The experimental feasibility study described by Garcia et al. requires several different test systems, and does not provide an indication of the depth at which corrosion is prevalent.

Thus, a simple method is needed to allow corrosion to be detected in vertical or near-vertical metal structural members extending into the ground.

SUMMARY OF THE INVENTION

To meet the need mentioned above, a method of mapping voltage potential along a metal structural member extending underground through a range of depths is described in accordance with the present invention. The method comprises the steps of providing a voltage meter having a positive terminal and a negative terminal, a reference electrode connected to the positive terminal, and a portable half-cell connected to the negative terminal; forming at least one hole in the ground that extends generally alongside the structural member and is spaced from the structural member; contacting the reference electrode with the structural member at an aboveground location on the structural member; and positioning the, half-cell at a series of test points in the hole or holes and operating the voltage meter to take a series of voltage potential measurements respectively corresponding to the series of test points, wherein the test points are located at different depths. Preferably, the method further comprises the step of plotting test point depth versus voltage potential.

Where ground conditions permit, it is most efficient to drill a single hole extending generally parallel to the structural member and insert the portable half-cell to different depths within the hole to take the measurements. More specifically, the hole could be drilled in stages to different measurement depths rather than all at once. Alternatively, where soil conditions are rocky or otherwise troublesome in the vicinity of the metal structural member, multiple holes may be formed equidistant from the structural member. In this regard, Applicants disclose a novel drill bit used to drill through earth for practicing the method of the present invention. The drill bit is a hybrid between a common wood-boring auger shank and a flat masonry-style drill bit tip. The tip acts to insinuate itself between rocks that are encountered as the hole is drilled, while the wood-auger shank efficiently removes soil material from the hole. The drill bit is preferably adjustable in length, such as by providing one or more shank extensions.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
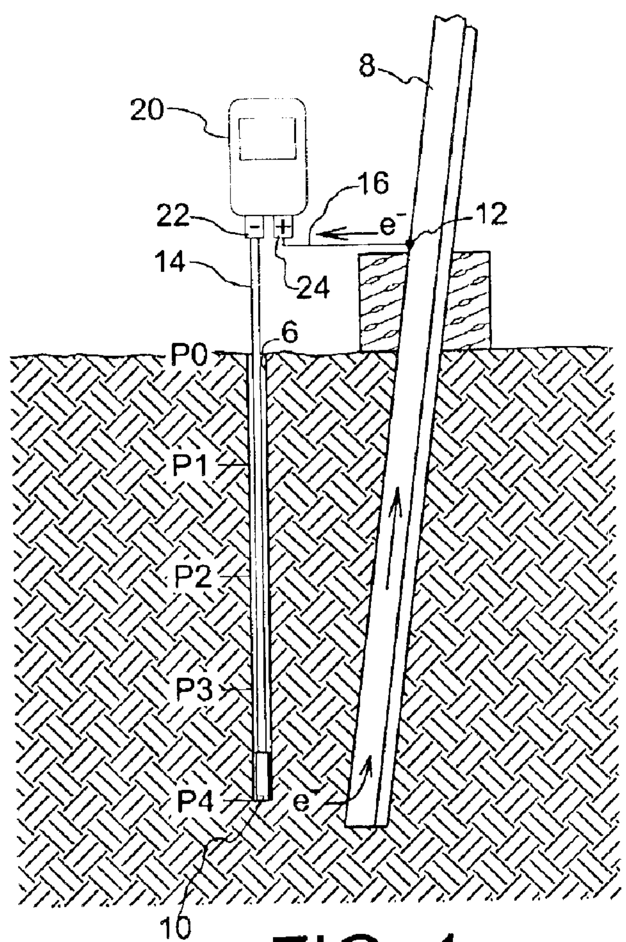
FIG. 1 is a schematic view illustrating a method of voltage potential mapping according to an embodiment of the present invention, wherein the method is applied with respect to a leg of a power transmission line tower.

Referring initially to FIG. 1 of the drawings, an elongated metal structural member 8 extends into the ground at a nearly vertical angle to a given depth. Structural member 8 may be a footing of a transmission line support tower or some other structural member extending underground through a range of depths, thereby making the member susceptible to corrosion. To map voltage potential along the buried length of structural member 8, a voltage meter 20 is provided having a negative terminal 22 and a positive terminal 24. Also provided for the purpose of mapping voltage potential is a half-cell electrode 10 connected to negative terminal 22 by an elongated probe 14, and a reference electrode 12 connected to positive terminal 24 by conducting line 16. Half-cell 10 is preferably a commercially available Cu/$CuSO_4$ half-cell, and reference electrode 12 can be in the form of an alligator clip or other configuration suitable for making contact with metal structural member 8.

In accordance with a method of the present invention, a hole 6 is formed through the ground at a location approximately two feet away from the location where structural member 8 enters the ground. It is preferred to form hole 6 so that it extends at least approximately parallel to structural member 8 in order to maintain a constant soil distance between hole 6 and the structural member along the buried length of the structural member. However, the true direction of the buried portion of a structural member may in some cases be unknown, and a vertical hole can be used as an approximation, as is shown in FIG. 1.

Voltage potential along structural member 8 is mapped by contacting reference electrode 12 with structural member 8 at an aboveground location on the structural member, positioning half-cell 10 at a series of test points P0–P4 at different depths in hole 6, and operating voltage meter 20 to take a series of voltage potential measurements respectively corresponding to the series of test points P0–P4. The number of test points and their spacing is a matter of choice, however it is contemplated to have a first test point P0 located at zero depth and successive test points at two-foot intervals along the axis of hole 6.

It is noted that hole 6 can be formed in one step to a suitable total depth, or in multiple stages to each successive test point. In the former approach, half-cell 10 must be arranged to contact the side wall of hole 6 facing structural member 8, except for a test point at the bottom of the hole where the half-cell could be contacted with the bottom wall of the hole. In the latter approach, half-cell 10 can be contacted with the bottom wall of the hole 6 at each successive stage of hole formation. It is further noted that multiple holes 6 may be formed about structural member 8 to different depths, however this is not preferred because it is more time consuming and can introduce variation in the measurements unrelated to corrosion. However, this approach may become necessary where a rocky impediment prevents a hole from being formed or continued along a chosen axis.

Figure 3:
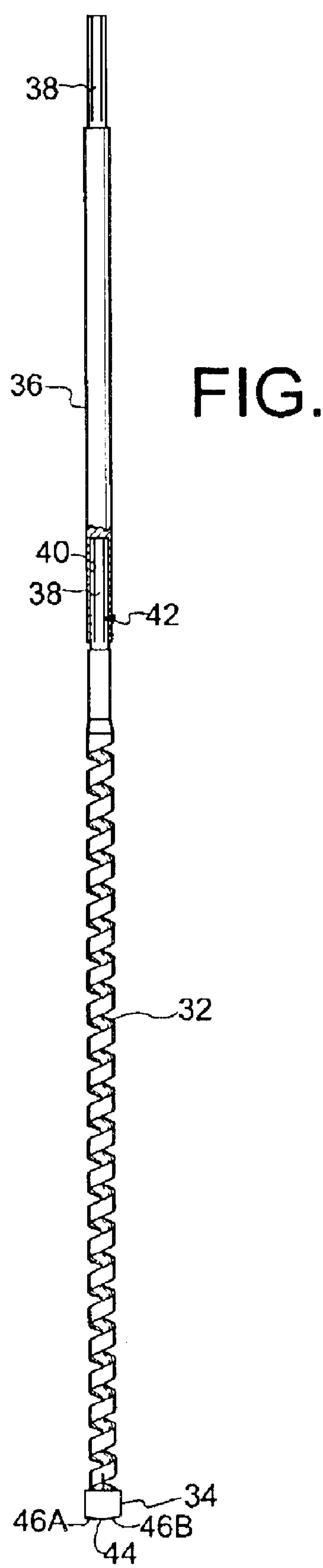
FIG. 3 is a side view of a novel drill bit used in practicing the method of the present invention.
Figure 4:
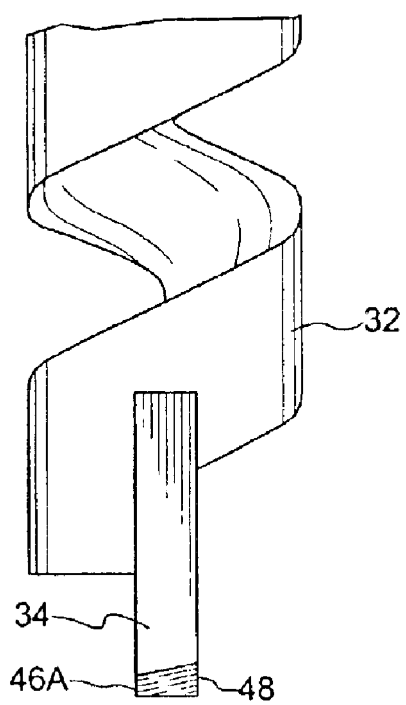
FIG. 4 is an enlarged detailed view of a tip of the drill bit shown in FIG. 3, wherein the drill bit has been rotated by ninety degrees from its rotational orientation shown in FIG. 3.

In order to form a hole 6 through varied soil conditions, a novel hybrid drill bit 30 has been developed as illustrated in FIGS. 3 and 4. Drill bit 30 is intended for use with a power drill having a chuck for holding the drill bit. Drill bit 30 generally comprises a shank 32 in the form of a wood-boring auger extending along a rotational axis of the drill bit, and a flat tip 34 in the form of a masonry drill bit tip. Tip 34, which is preferably coated with or formed of a hard material such as a carbide alloy, has a central nose 44 and pair of leading edges 46A and 46B on opposite sides of the bit's rotational axis. Nose 44 is defined by an included angle greater than ninety degrees, and preferably about one-hundred thirty-five degrees. As seen in FIG. 4, a slight relief angle is provided from leading edge 46A to a trailing edge 48 of the tip such that the leading edge is slightly lower than the trailing edge. A similar trailing edge and relief angle, not visible, are provided on the opposite side of tip 34 with respect to leading edge 46B. As mentioned above, tip 34 acts to insinuate itself between rocks that are encountered as the hole is drilled, while the wood-auger shank efficiently removes soil material from the hole.

Drill bit 30 is preferably adjustable in length, such as by providing one or more shank extension segments. Drill bit 30 is extendable by use of one or more extensions 36 having an axially extending opening 40 at one end that is shaped to receive a chuck end 38 of the drill bit, and a replacement chuck end 38 at its opposite end. The chuck ends 38 and opening 40 may be hexagonal or otherwise include at least one flat surface to prevent rotation relative therebetween. The original chuck end 38 of drill bit 30 is provided with a keyway or the like for receiving a radially extending set screw 42 for releasably holding the original chuck end 38 within opening 40. In a working embodiment, the auger shank 32 is three-quarters of an inch in diameter and tip 34 is one inch wide.

Figure 2:
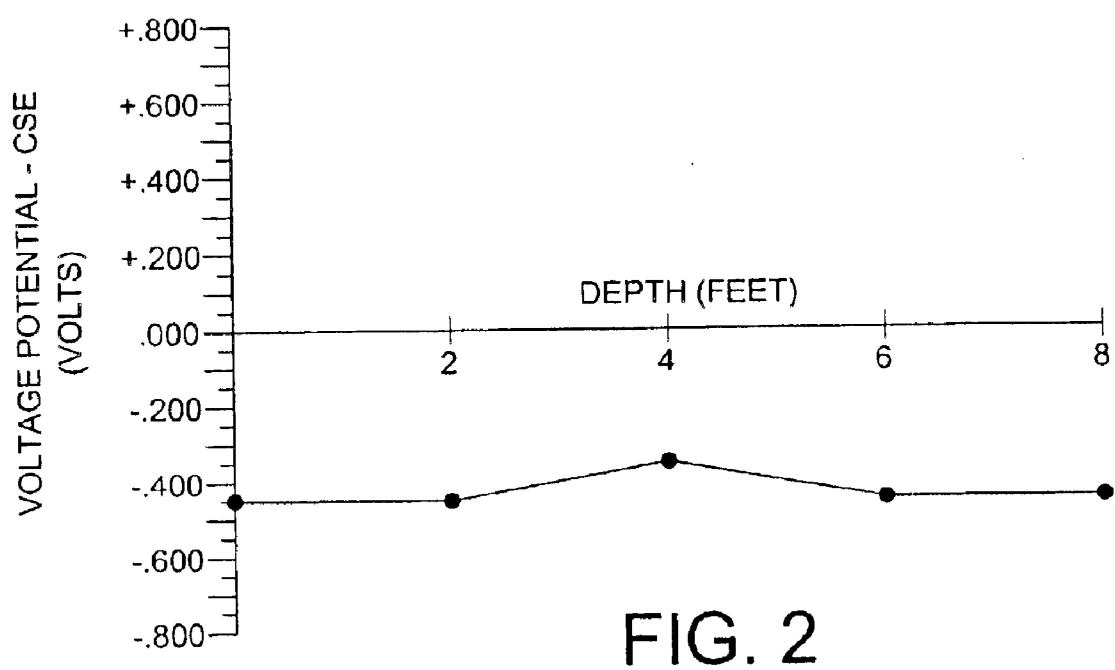
FIG. 2 is a graph of voltage potential versus depth obtained by the method of the present invention, wherein the tested structural member exhibits signs of localized corrosion.

Attention is now directed to FIG. 2 of the drawings, which shows a graph of measured voltage potential versus depth with respect to a steel structural member without cathodic protection (CP). As can be seen, a peak or anomaly occurs at four feet of depth, indicating a possible location of corrosion concern. In this case, crews may decide to partially unearth the structural member to check and treat the member at a depth of about four feet, rather than digging to expose the entire buried portion of the structural member, thereby saving time and resources. Thus, the method of the present invention helps to pinpoint corrosion in structural members extending vertically or near vertically underground.

What is claimed is:

1. A method of mapping voltage potential along a metal leg of a power line transmission tower, wherein said leg extends underground in a substantially vertical direction, said method comprising the steps of:

providing a voltage meter having a positive terminal and a negative terminal, a reference electrode connected to said positive terminal, and a portable half-cell connected to said negative terminal;

forming at least one hole in the ground, said at least one hole extending generally alongside said leg and being spaced from said leg;

contacting said reference electrode with said leg at an aboveground location on said leg; and positioning said half-cell at a series of test points in said at least one hole and operating said voltage meter to take a series of voltage potential measurements respectively corresponding to said series of test points, wherein said test points are located at different depths.

2. The method according to claim 1, further comprising the step of plotting test point depth versus voltage potential.

3. The method according to claim 1, wherein said series of test points are separated by a regular depth interval.

4. The method according to claim 1, wherein said at least one hole is a single hole.

5. The method according to claim 4, wherein said single hole is formed in stages and a voltage potential measurement is taken after each stage.

6. The method according to claim 1, wherein said at least one hole is a plurality of holes arranged about said leg and formed to different depths.

7. The method according to claim 1, wherein said step of forming said at least one hole is performed using a drill and an adjustable length drill bit.

* * * * *